United States Patent [19]

Jensen et al.

[11] 4,232,001
[45] Nov. 4, 1980

[54] METHODS AND MATERIALS FOR DETECTION OF ESTROPHILIN

[75] Inventors: Elwood V. Jensen; Eugene R. DeSombre, both of Chicago, Ill.

[73] Assignee: University Patents, Inc., Norwalk, Conn.

[21] Appl. No.: 945,000

[22] Filed: Sep. 22, 1978

[51] Int. Cl.$^2$ ...................... G01N 33/16; A61K 43/00
[52] U.S. Cl. ........................................ 424/1; 23/230 B; 260/112 B; 424/12
[58] Field of Search .................... 424/1, 12; 23/230 B; 260/112 B

[56] References Cited

U.S. PATENT DOCUMENTS

| | | | |
|---|---|---|---|
| 4,132,767 | 1/1979 | Tohmatsu et al. | 424/1 |
| 4,152,410 | 5/1979 | Ishii | 424/1 |
| 4,160,817 | 7/1979 | Bucouaz et al. | 424/1 |

OTHER PUBLICATIONS

Mercier-Bodard et al., Chem. Abstracts, vol. 89, Sep. 11, 1978, #86004b.
Woods et al., Chem. Abstracts, vol. 88, Feb. 13, 1978 #48714e.

*Primary Examiner*—Benjamin R. Padgett
*Assistant Examiner*—Christine M. Nucker
*Attorney, Agent, or Firm*—Merriam, Marshall & Bicknell

[57] ABSTRACT

Antibodies specifically immunologically reactive with estrophilin. Methods and materials for detection and quantification of estrophilin in tissue samples, notably those of human breast cancer tissue.

8 Claims, No Drawings

METHODS AND MATERIALS FOR DETECTION OF ESTROPHILIN

The invention described herein was made in the course of work under a grant or award from the Department of Health, Education and Welfare.

BACKGROUND

The present invention relates generally to antibodies for estrogen receptor protein and the in vitro detection and quantification of such protein through use of such antibodies. More specifically, the invention provides novel antibody preparations which have specific reactivity with estrogen recepetor and improved test methods and reagents for detection and quantification of receptor protein by means of immunological reactions.

It is generally recognized that specific estrogen-binding proteins, called "estrogen receptors" or, generically, "estrophilin" are responsible for the uptake of estrogenic hormones by certain tissues. The hormones are believed to interact with extranuclear estrophilin present in hormone dependent or "target" cells, with the "activated" estrogen-receptor complex so formed being translocated to the cell nucleus where it binds to the chromatin and in some way enhances the ability of the nucleus to synthesize certain types of RNA.

It has been determined that certain tissues, notably certain human breast cancer tissues, are estrogenic hormone "dependent" in the sense that systemic deprivation of supportive estrogen will result in regression of tissue growth and cell proliferation. As one example of this dependence, bilateral adrenalectomy can effect striking remission of advanced breast cancer in postmenopausal women and similar remissions are observed after hypophysectomy. Estrogen deprivation by surgical ablation of tissue responsible for estrogen production and/or endocrine additive therapy afford the most effective treatments presently available for advanced breast cancer. Unfortunately, less than one-half of the premenopausal patients and even a smaller fraction of postmenopausal patients respond to this type of therapy—indicating that breast cancer tissue is not always of the cellular type which is estrogenic hormone dependent. Consequently, it is significant to the prognosis and treatment of human breast cancer to be able to ascertain whether excised tumor tissue of a breast cancer patient is comprised predominantly of estrogen dependent cell types. On the basis of such information, a reasonable ablation response prediction may be made. Surgical removal of estrogen producing glands for the purpose of estrogen deprivation may be restricted to those patients most likely to be helped by the procedure. Correlatively, other breast cancer patients can be spared the trauma of essentially useless surgery and may be placed immediately into alternative therapeutic programs such as radiation or chemotherapy.

Heretofore, the presence of estrogen dependent tissue in mammary tumor samples has principally been determined by quantitative detection of estrophilin in the sample through radiochemical assay. According to one such procedure developed by the inventors and their co-workers, radioactive (e.g., tritiated) estradiol is added to the cytosol—or supernatant fraction—of a homogenized tissue sample, and the tritiated estradiol reversibly combines with any estradiol-receptor protein present in the cytosol. The specimen is then subjected to low-salt, sucrose density gradient ultra-centrifugation and the protein-estradiol complex, being a large molecule, sediments with a characteristic velocity. A radioactive count can be used to quantify the complex. [See, e.g., Jensen, et al., J. Steroid Biochem., 7, 911–917 (1976); see also, Jensen, et al., "Estrogen Receptors and Breast Cancer Response to Adrenalectomy," National Cancer Institute Monograph, 34, 55–77 (1971)]. This procedure is carried out in the presence and in the absence of an inhibitor of the desired specific binding in order to identify and exclude any binding that is non-specific. The above analytical technique requires use of rather sophisticated, costly and uncommon ultracentrifugation apparatus, the operation of which requires a high degree of skill on the part of the laboratory worker. Other methods employed for receptor assays have similar limitations. [See, e.g., Korenman et al., J. Clin. Endocrinol. & Metab. 30, 699–645 (1970)] As a result, despite the exceptional usefulness of quantitative detection of estrophilin in prediction of response to endocrine therapy, the utilization of prior radiochemical assays is limited by scientific, geographic, and economic considerations.

It has long been recognized that immunochemical techniques for estrophilin detection would, if available, provide a simpler and less costly analytical procedure which would be susceptible to more widespread clinical use. Although suggestive evidence for the presence of antibodies to estrogen receptor in the serum of animals injected with partially purified estrophilin preparations has been reported [See, e.g., Soloff, et al., Biochem. Biophys. Res. Comm., 34, 141–147 (1969); Fox, et al., FEBS Lett., 63, 71–76 (1976); and Jensen, et al., Arch. Anat. Microscop. Morph. Exptl., 56 Suppl., 547–569 (1967)], the art has heretofore not been provided with any definitive demonstration that antibodies to estrophilin can be generated, prepared in quantity, and effectively employed in an assay for estrophilin—especially in tissue of differing species. Indeed the expectancy for success in the search for antibodies to estrophilin has been substantially diminished by past failure of allegedly highly purified progesterone receptor from oviduct tissue to give any trace of immune response in rabbits. Such findings have been supportive of wholly non-immunogenic characteristics for the proteinaceous steroid hormone receptors generally, and for estrophilin in particular.

BRIEF SUMMARY

According to the present invention there is provided for the first time a high yield of well-defined antibody isolate to estrophilin. More specifically, immunoglobulin obtained from the serum of animals immunized with a highly purified preparation of estradiol-receptor complex from calf uterine nuclei has been demonstrated to contain specific anti-estrophilin by five criteria: (1) precipitation of radioactive estradiol-recetor complex upon addition of heterologous species antibody (against the immunoglobulin of the immunized animal) to a mixture of the tritiated estradiol-receptor complex and the immunoglobulin; (2) adsorption of the estradiol-receptor complex by the immunoglobulin linked to a supporting polymer; (3) adsorption of the estradiol-receptor complex in the presence of the immunoglobulin by *Staphylococcus aureus* protein-A linked to a supporting polymer; (4) the ability of the immunoglobulin to increase the sedimentation rate of the estradiol-receptor complex; and (5) the ability of the immunoglobulin to modify the elution characteristics of estrophilin on gel filtration.

The purified preparation of estradiol/estrophilin complex employed for immunization according to the present invention is obtained by ammonium sulfate precipitation, gel filtration, and electrophoretic separation.

A further aspect of the present invention comprises a novel immunochemical procedure for quantitative detection of estrophilin in small amounts of tissue specimen, notably breast cancer tissue, through use of the above-mentioned antibody preparations. More specifically, according to procedures of the invention specific anti-estrophilin of the invention are cross-reacted with a preparation of body tissue such as mammary tumor tissue which is suspected to contain estrophilin in relatively large quantities. The reaction product so obtained is subjected to chemical, physical or radiological examination capable of quantifying the estrophilin in the sample. One preferred procedure involves treatment of a body tissue with, e.g., tritiated estradiol to form an estradiol/estrophilin complex, followed by contact with an antibody supporting or containing reagent. The quantity of estrophilin in the sample is determined by analysis of the immunologically-bound complex of estradiol/estrophilin/anti-estrophilin through scintillation counting or the like. According to another procedure, immunologically inert, but chemically or radiologically marked, particles have surface portions sensitized with the antibody preparation and are contacted with the tissue sample, with estrophilin quantified on the basis of agglutination phenomena. Agglutination phenomena of sensitized particles in contact with an estrophilin-containing specimen may also be monitored by other techniques (e.g., turbidometric techniques). Immunohistochemical procedures involving fluorescent or peroxidase coupled anti-estrophilin preparations are also made available by the invention.

Reagents prepared according to the invention include immunologically inert particles, surface portions of which are sensitized with specific antibody preparations of the invention.

Further aspects and advantages of the invention will become apparent to those skilled in the art upon consideration of the following detailed description of presently preferred embodiments thereof.

DETAILED DESCRIPTION

The following description includes use of certain abbreviations: "E*" shall mean tritiated estradiol; "R" shall mean estrophilin; "E*R" or "E*R complex" shall designate the radioactive complex of estradiol and estrophilin; "Ig-i" shall designate the immunoglobin fraction obtained from serum of an animal immunized with E*R; and "Ig-n" shall designate immunoglobin from serum of a nonimmunized animal.

The reagents employed in certain of the illustrative examples include the following. [6,7-$^3$H] Estradiol-17$\beta$ (57 Ci/mmol) and [2,4,6,7-$^3$H]estradiol-17$\beta$(108 Ci/mmol) were obtained from New England Nuclear Co. and, unless otherwise noted, E* represents the 6,7-tritiated hormone. Tubercle bacilli and Freund's complete and incomplete adjuvants were purchased from Difco, bordetella pertussis vaccine from Eli Lilly & Co., and *Staphylococcus aureus* protein-A bound to Sepharose CL-4B from Pharmacia. Immunoglobulin from immunized and nonimmunized rabbits was coupled to cyanogen bromide-activated Sepharose 4B by the procedure of Cuatrecasas, et al., "Affinity Chromatography" in *Methods in Enzymology*, (Academic Press, New York) Vol. 22, pp. 345-378 (1971). Antiserum to rabbit Ig was prepared by immunizing a female goat with purified rabbit immunoglobulin (12.5 mg for primary injection; 5-12 mg for booster injections) in a manner similar to that described for immunization of rabbits with E*R except that the emulsion containing the antigen was injected subcutaneously. Unless otherwise noted, phosphate buffers were prepared from sodium salts, and all buffers contained 0.01% (wt/vol) sodium azide. Phosphate-buffered saline contained 150 mM sodium chloride in 10 mM phosphate, pH 7.8. Buffers using Tris (T), pH 7.4 at 23° sometimes containing potassium chloride (K) and disodium EDTA (E), are designated according to the millimolarity of their components; e.g., $T_{10}K_{400}E_{1.5} = 10$ mM Tris/400 mM KCl/1.5 mM EDTA.

EXAMPLE 1

Preparation of Purified Estradiol-Receptor Complex (E*R)

The estradiol-receptor protein in the form of an estradiol-receptor complex which is capable of inducing formation of an antibody having a specific reactivity with the estradiol-receptor protein in an immunological reaction was prepared according to a modification of the method of Gorell, et al., "Purification of Nuclear Estrogen Receptors" in *Proceedings of the Fifth International Congress of Endocrinology*, (Excerpta Medica Foundation, Amsterdam) Vol. 1, pp. 467-472 (1977). Unless otherwise noted, all procedures were carried out at 0°-2° C.

A calf uterine homogenate in $T_{10}$ buffer was centrifuged at 10,000×g to separate the cytosol from crude nuclear sediment. The cytosol was treated with 30 nM E* (5.7 Ci nmol.). One-fifth of the sediment was washed successively with $K_{400}T_{10}$, pH 7.9, and $T_{10}$, pH 7.5, and then resuspended in the cytosol. After incubation of the stirred mixture at 25° C. for 60 minutes, the nuclear sediment was collected by centrifugation, washed with $T_{10}$ buffer and extracted with $K_{400}T_{10}$ buffer. The extracted receptor complex was precipitated with ammonium sulfate (30% of saturation) and redissolved in $K_{400}T_{25}$, pH 7.5, (0.1 volume of the original extract) by gentle homogenization followed by stirring for 20 minutes. After clarification by centrifugation at 98,000×g for 60 minutes, the solution was subjected to gel filtration on Sephadex G-200 (Regular grade, Pharmacia) in $K_{400}T_{25}$ buffer. The estrogen receptor complex (determined by radioactivity assay) separated from the bulk of other proteins (determined by optical density at 280 nm) which eluted in the void volume. The pooled receptor-containing fractions were concentrated first by ultrafiltration with XM-50 membrane (Amicon) and further by salt precipitation with ammonium sulfate (30% of saturation). The receptor complex was redissolved in $K_{30}T_{10}$, pH 7.5, and subjected to polyacryamide gel electrophoresis using 0.7 centimeter diameter, 5% or 7% acryamide gel with 2.5% cross-linkage prepared in Tris-HCl buffer pH 8.9. The electrophoresis is carried out with a current of 3 milliamps per gel, using electrode buffers of Tris-glycine, pH 8.3, or Tris-borate, pH 8.6 The receptor protein was isolated by slicing the gels, extracting the pooled gel slices with 10 nM sodium phosphate buffer, pH 7.4, (0.1 ml per slice) and combining the fractions with the highest radioactivity ($R_f$=0.45 for 7% gels; $R_f$=0.60 for 5% gels). The pooled extract was dialyzed against $K_{10}T_{10}$ (azide-free), pH 7.5, and lyophilized to dryness.

The product has an isoelectric point of about 6.0, shows a single stained protein band on acrylamide gel electrophoresis, and analytical ultracentrifugation indicates a single ultraviolet absorbing macromolecular species. Elution from a calibrated Sephadex G-200 column indicates a Stokes radius of 36.5, corresponding to a molecular weight of about 66,000 daltons.

EXAMPLE 2

Preparation of Antibodies for Estradiol Receptor Protein

Antibody preparations having specific reactivity with estrophilin protein are obtained by immunizing rabbits or like mammals with the purified E*R complex of Example 1 according to the procedure described by Vaitukaitis, et al., J. Clin. Endocrinol. Metab. 33, 988–991 (1971). For the primary immunization of six month-old male New Zealand White rabbits, an emulsion, prepared by homogenizing a saline solution containing 20 $\mu$g of the E*R with an equal volume of Freund's complete adjuvant and an additional 5 mg of dried tubercle bacilli, was injected intradermally at multiple sites on the back, while 0.5 ml of bordetella pertussis vaccine without added antigen was injected in the thigh. Six booster injections were given over a period of one year with an emulsion of the immunogen and Freund's incomplete adjuvant; the last two booster injections, containing 20 and 50 $\mu$g of receptor, respectively, were given about 45 days, and 15 days before collecting the blood from the marginal ear vein of the rabbit. A crude immunoglobulin fraction (Ig-i) was prepared from the serum by precipitation with 33% saturated ammonium sulfate in 50 mM phosphate buffer, pH 7.4, according to the procedure of Shiu, et al., Biochem J., 157, pp. 619–625 (1976). The washed precipitate was redissolved in phosphate-buffered saline (or in some experiments in 20 mM phosphate, pH 7.4) and the dialyzed solution, after clarification by centrifugation, was analyzed for protein by its absorbance at 280 nm and for the absence of other serum proteins by acrylamide gel electrophoresis. Immunoglobulin (Ig-n), prepared similarly from serum of nonimmunized animals (as well as from the immunized animals before any antibody titer appeared), was used as a control.

EXAMPLE 3

Preparation of Hormone-Receptor Complexes

Estradiol-receptor complexes of uterine cytosols from immature calves, rats, mice, and guinea pigs were prepared by homogenizing the tissues in four volumes of $T_{10}$ buffer, using a Polytron PT-10 homogenizer with efficient cooling, and making the high-speed supernatant fraction 20 nM in E*, after 60 minutes at 4° the excess E* was removed with dextran-coated charcoal. A complex of human breast cancer cytosol was prepared similarly except that the tumor specimen, pulverized while frozen in liquid nitrogen, was homogenized in $T_{10}$ containing 0.5 mM dithiothreitol, and the cytosol fraction was made 0.5 nM in E* (108 Ci/mmol) without the use of charcoal. Crude nuclear complex of calf uterus was prepared by extraction of washed nuclear sediment with $T_{10}K_{400}$ after its incubation for 60 minutes at 25° with 20 nM E* in calf uterine cytosol. Rat nuclear complex was obtained by similar extraction of the nuclear sediment from a homogenate in $T_{10}$ of immature rat uteri excised 4 hours after the subcutaneous injection of 100 ng (20.8 $\mu$Ci) of E* in 0.2 ml of saline.

EXAMPLE 4

Immunochemical Interaction Studies

For double antibody precipitation of the crude estradiol-receptor complexes, a solution of E*R (1.0 pmol), normal rabbit serum (10 $\mu$l), and immunized rabbit serum (10 $\mu$l) in 1.0 ml of phosphate-buffered saline containing 10 mM EDTA was incubated at 4° for four hours, after which sufficient goat antiserum against rabbit Ig was added to precipitate all the rabbit Ig. Controls used 20 $\mu$l of normal rabbit serum and no immunized rabbit serum. After 16 hours the mixtures were centrifuged and the pellets were dissolved in 100 $\mu$l of 0.1 M NaOH; radioactivity was measured in 10 ml of scintillation mixture containing 10 mM HCl.

For immunoadsorption experiments, a solution of 0.8 pmol of E*R or E* was incubated for four hours at 4° with an agitated suspension of either Sepharose-Ig-i or Sepharose-Ig-n (containing 300 $\mu$g of protein) or of Sepharose alone in a total volume of 600 $\mu$l of $T_{10}K_{400}$. Similarly, 0.3-pmol aliquots of E*R or E* in $T_{10}K_{400}$ were incubated at 4° for 90 minutes with 100 $\mu$g of either Ig-i or Ig-n (or with no added immunoglobulin) and then for four hours longer with an agitated suspension of 50 $\mu$l of Sepharose-protein-A in a final volume of 500 $\mu$l of $T_{10}K_{400}$. After centrifugation, the beads were washed and the combined supernatant and washings were assayed for radioactivity in Triton X-100 scintillation mixture.

EXAMPLE 5

Sedimentation Studies

Various hormone-receptor complexes (0.05–2 pmol in 150 $\mu$l of $T_{10}$ cytosol or $T_{10}K_{400}$ nuclear extract) and Ig-i or Ign-n (usually 200 $\mu$g) were incubated at 4° for 1–5 hours in a final volume of 220 $\mu$l of $T_{10}$ or $T_{10}K_{400}$ depending on the gradient to be used. A 200-$\mu$l aliquot of each mixture was layered on 3.5 ml of a 10–30% sucrose gradient containing either $T_{10}K_{10}E_{1.5}$ (low salt) or $T_{10}K_{400}E_{1.5}$ (high salt) and centrifuged at 2° for 16 hours at 253,000×g. Successive 100-$\mu$l fractions were collected from the bottom and radioactivity was measured in Triton X-100 scintillation mixture. In some studies bovine plasma albumin (4.6 S), bovine gamma globulin (7.0 S), $\beta$amylase (9.2 S), and catalase (11.3 S) were sedimented in parallel gradients to serve as markers.

EXAMPLE 6

Gel Filtration Studies

Gel filtration studies were carried out with the calcium-stabilized form of the cytosol estrogen receptor complex obtained by homogenizing calf uterus in $T_{10}E_{1.5}$ and incubating the cytosol fraction with 1 M KCl and 4 mM $CaCl_2$, with or without 20 nM E*, for 60 minutes at 4° C. After precipitation with ammonium sulfate (25% of saturation) the receptor (R) or estrogen-receptor complex (E*R) was dissolved in $T_{10}K_{400}$ and clarified by centrifugation at 250,000×g for 30 minutes.

For gel filtration experiments aliquots of E*R or R (5 pmol) and Ig-n or Ig-i (1.0 mg) were incubated for 60 minutes at 4° C. and then filtered through Sephadex G-200 columns (0.9×55 cm) equilibrated in $T_{10}K_{400}$. Fractions (0.3 ml) were collected and either assayed for radioactivity or (in the case of materials derived from cytosol fractions not incubated with E*) treated with E* and then dextran coated charcoal to remove excess E*. The latter procedure resulted in a material then assayed for radioactivity. The void volume of the column was determined with blue dextran. Bovine serum albumin and rabbit immunoglobulin were employed as markers.

The results of the above-described immunochemical, sedimentation and gel filtration studies demonstrated that immunoglobulin from the serum of a rabbit immunized with purified estrogen receptor complex of calf uterine nuclei contains specific antibodies to the estrophilin receptor protein. As shown in the accompanying Table 1, in the presence of Ig-i, but not of Ig-n, a significant amount of tritiated estradiol in the form of E*R complex is precipitated by antiserum to rabbit gamma globulin or bound to *Staphylococcus aureus protein-A*, a substance that reacts specifically with the IgG type of antibody. Similarly, Ig-i linked to Sepharose binds a much greater proportion of tritiated estradiol/estrophilin (E*R) complex than does Sepharose-Ig-n or Sepharose alone.

TABLE 1

| | Interaction of rabbit Ig with E*R complexes of calf uterus | | | |
|---|---|---|---|---|
| | | % E* precipitated or bound | | |
| Method | Form of Estradiol | Ig-i | Ig-n | NoIG |
| Double antibody precipitation | E*R nuclear | 61 | 10 | |
| | E*R cytosol | 56 | 3 | |
| | E* | 2 | 2 | |
| Binding to Sepharose-Ig | E*R nuclear | 66 | 21 | 17 |
| | E* | 6 | 15 | 7 |
| Binding to Sepharose-Protein-A | E*R nuclear | 70 | 17 | 30 |
| | E* | 3 | 5 | 3 |

From sedimentation studies, it was found that addition of Ig-i, but not of Ig-n, causes an increase in the sedimentation velocity of the purified 4.8 S E*R complex used as the antigen in the immunization.

Sedimentation patterns reveal that the above-described antibody preparation derived through use of estrophilin from calf uterus is cross reactive with estrogen receptor complexes from rat, mouse, and guinea pig uteri and from human breast cancer. Significantly, however, the failure of the anti-estrophilin preparations to react with the dihydrotestosterone-receptor of rat prostate or the progesterone receptor of chick oviduct, shows a specificity of the antibody for estrophilin protein.

Gel filtration studies verified that Ig-i but not Ig-n reacts with both the E*R and R forms of estrogen receptors as demonstrated by a shift of elution to the void volume on the column (Sephadex G-200). For the uncomplexed receptor, the eluted R/IG-i complex could be labelled with E* to form E*/R/Ig-i, demonstrating that the complexing of the estradiol hormone with the receptor does not block the binding site of estrophilin.

In sum, immunoglobulin obtained from the serum of rabbits immunized with a highly purified preparation of E*R complex from calf uterine nuclei is shown to contain specific antibodies to estrophilin by five criteria: (1) precipitation of the radioactive steroid upon addition of goat antibody against rabbit immunoglobulin to a mixture of the tritiated estradiol-receptor complex and the immunoglobulin, (2) adsorption of the estradiol-receptor complex by the immunoglobulin linked to a polymer support, e.g., Sepharose, (3) adsorption of the estradiol-receptor complex in the presence of the immunoglubulin by *Staphylococcus aureus protein-A linked to a polymer support, e.g., Sepharose;* (4) the ability of the immunoglubulin to increase the sedimentation rate of the estradiol-receptor complex; and (5) the ability of the immunoglobulin to modify elution characteristics of estrophilin on gel filtration. The antibodies cross-react with the nuclear receptor of calf, rabbit, sheep and rat uterus, as well as with the extranuclear receptor of calf, rat, mouse, guinea pig, sheep, and rabbit uterus. Cross-reactivity is also observed with nuclear receptor of MCF-7 (human breast cell) and rat endometrial tumors as well as with extranuclear receptor of rat breast, human breast, MCF-7 breast, rat endometrial, and rat pituitary tumors.

The antibodies do not react with either the nuclear or extranuclear dihydrotestosterone-receptor complexes of rat prostate or with the extrauclear progesterone-receptor complex of chick oviduct, rabbit uterus and rat endometrial tumor.

The cross-reactivity of the anti-estrophilin (Ig-i) with estrophilin from human breast cancer makes possible the use of simple immunoassays including radioimmunoassays for the estradiol-receptor protein content of breast cancer tissue as a guide to endocrine therapy.

The reaction of anti-estrophilin prepared according to the invention with uncomplexed receptor (R) is indicated by the ability of R to compete with E*R for a limiting amount of antibody. This type of analysis revealed that, whether complexed with estradiol or not, calcium-stabilized estrophilin from calf uterine cytosol shows essentially identical competition with radioactive cytosol receptor complex for the antibody, although somewhat less than that shown by receptor from rat endometrial tumor. On the basis of this finding, a simple immunoassay for estrophilin in extracts of tissue homogenates is available—limited only by the relatively low radioactivity of the tritiated estradiol marker. Some increase in sensitivity may be gained through use of hexatritiated estradiol and, of course, radiodinated receptor and/or antibody would be most useful in such an assay.

According to the invention novel immunological reagents are provided when the immunoglobulin fraction of serum of an animal immunized with purified estrophilin estradiol complex is employed, with or without prior treatment to remove non-specific antibodies in the immunoglobulin, to sensitize immunologically inert particulate materials such as stabilized erythrocytes (e.g., prepared according to the procedures of U.S. Pat. Nos. 3,714,345; 3,715,427; and/or 3,924,541), bentonite, collodion, crystalline cholesterol, quartz, synthetic resins, various kinds of synthetic latex (see, e.g., U.S. Pat. No. 3,551,555), or liposomes prepared from phospholipids and sterols including radioactive material-containing or free radical-containing liposomes. Such sensitized particles are useful when employed in direct agglutination assays wherein estrophilin or estrophilin radioisotopic estradiol complex in a tissue sample will be bound to and effect agglutination of the particles, allowing quantification of the complex by standard radioimmunoassay techniques. Alternatively, when antibody materials are employed to sensitize radioactive material or free radical-containing particles, estrophilin content of a tissue sample homogenizate may be determined by adding such particles to the sample, withdrawing particles agglutinated by the estrophilin and "counting" the particles as aggregated. Further, techniques using radiochemically-labelled, or enzyme-linked, or otherwise detectable anti-estrophilin may provide the basis for estrophilin assays that do not detect the complex formed by binding with estradiol (E*). Substantial advantages are expected to accompany procedures which are independent of the reversible binding of estrophilin in the sample to radioactive estradiol. In particular, such procedures should be able to detect the amount of free estrophilin as well as estrophilin already associated with non-radioactive, endogeneous estradiol.

In one such further application, anti-estrophilin provides the basis for a specific immunohistochemical procedure for the detection and quantification of estrogen receptor in pathologic sections of cancer tissue. Such sections are incubated with solutions of the antibody and, after washing with buffer, incubated either with fluorescent-labelled second antibody (to the immunoglobulin) or with peroxidase-antiperoxidase-complexed second antibody. After further washing, the sections are examined for the presence of estrophilin by fluorescent microscopy, or after peroxidase staining, by light microscopy. This technique allows the detection of estrophilin in tissue sections carried out in the same surgical pahological laboratory where the cancer diagnosis is made.

Numerous modifications and variations of the invention are expected to occur to those skilled in the art upon consideration of the foregoing detailed description. While the above-described preferred embodiment of procedures for preparing and isolating anti-estrophilin represents the best mode presently available for effecting isolation of the antibody substances in their purest form, other techniques are certainly within the contemplation of the invention. As one example, lymph node cells from rabbits immunized with the purified E*R complex may be fused with mouse myeloma cells in the presence of polyethylene glycol, generally according to the technique of Milstein [Kohler and Milstein, 256, 495–497 (1975)] The surviving hybrids would then be screened by selective cloning to obtain only cells which produce the anti-estrophilin antibody substance. The cell line(s) so obtained would be grown in suspension culture to provide substantial quantities of anti-estrophilin which, when separated from contaminating myeloma antibody by immuno-absorption, may be employed as noted above in immunoassay techniques for quantitative detection of estrophilin in a tissue sample.

The availability of monospecific anti-estrophilin provided by the invention is expected to make possible further developments is diagnosis of breast cancer and other cancer tissues which contain estrophilin. Linkage of an isotope, (e.g., Iodine) or other radiologically detectable moiety to the specific anti-estrophilin would provide a basis for a new diagnostic scanning technique. After administration to a patient having an estrophilin-rich primary tumor, such a reagent has the potential to concentrate in a metastatic tumor site also containing estrophilin, causing metastases to be evident on an appropriate radiologic body scan.

Furthermore, since tumor components or their partial degradation components are often released into the blood, an assay for immunoreactive fragments of estrophilin in the sera of patients with (or suspected of having) an estrophilin-containing cancer could provide a means for early diagnosis of metastatic disease.

Consequently, only such limitations as appear in the appended claims should be placed upon the invention as above described.

What is claimed is:

1. A specific, immunologically active anti-estrophilin antibody obtained as a serum immunoglobulin component from an animal immunized with estrophilin, and characterized by its donation to the immunoglobulin of the following properties;
   (1) the ability to precipitate estrophilin from a mixture of estrophilin and said immunoglobulin upon addition of heterologous species antibodies to the immunoglobulin of the serum donor species;
   (2) the ability to mediate rapid absorption of estrophilin from a fluid by support polymer when said immunoglobulin is linked to the support polymer;
   (3) the ability of said immunoglobulin to mediate absorption of estrophilin from a fluid by $S.$ $aureus$ protein-A linked to a support polymer;
   (4) the ability of said immunoglobulin to increase the sedimentation rate of estrophilin; and,
   (5) the ability of said immunoglobulin to modify elution characteristics of estrophilin on gel filtration.

2. An immunological reagent comprising the anti-estrophilin antibody of claim 1 in combination with a radiologically detectable marker substance.

3. The reagent of claim 2 wherein the marker substance is tritiated estradiol.

4. An immunological reagent comprising the anti-estrophilin antibody of claim 1 and a plurality of immunologically inert particles, said substance providing an immunologically sensitive surface on said particles.

5. An immunological assay for estrophilin in a tissue sample said assay comprising contacting said sample with the reagent of claim 4 and quantitatively detecting the presence of estrophilin by monitoring agglutination behavior of said reagent particles.

6. An assay according to claim 5 wherein said tissue sample is a human breast cancer tissue sample.

7. The method for obtaining serum immunoglobin containing a specific anti-estrophilin antibody, said method comprising the steps of:
   preparing a purified complex of radioisotopic estradiol and estrophilin by incubating estrophilin-containing tissue in the presence of radioisotopic estradiol and isolating the complex from said incubate by precipitation, gel filtration and electrophoresis;
   inoculating an immunologically active animal with said complex and,
   isolating serum immunoglobin from said animal.

8. Anti-estrophilin antibody raised in tissue of animal origin against estrophilin of animal origin, said antibody characterized by being immunologically reactive with estrophilin of human breast cancer tissue.

* * * * *